United States Patent
Dubats

(10) Patent No.: US 6,968,845 B2
(45) Date of Patent: Nov. 29, 2005

(54) ADJUSTABLE STRAP FOR AMBULATOR

(76) Inventor: David E. Dubats, 2408 Avenue A, Bradenton Beach, FL (US) 34217

( * ) Notice: Subject to any disclaimer, the term of this patent is extended or adjusted under 35 U.S.C. 154(b) by 103 days.

(21) Appl. No.: 10/605,558

(22) Filed: Oct. 8, 2003

(65) Prior Publication Data

US 2005/0076920 A1   Apr. 14, 2005

(51) Int. Cl.[7] .............................................. A61F 5/37
(52) U.S. Cl. ................... 128/875; 128/876; 128/100.1; 128/101.1; 297/468
(58) Field of Search ................. 128/875, 876, 128/845, 846, 100.1, 101.1, 102.1; 602/36, 602/78; 297/468, 476, 479, 485; 2/338, 339

(56) References Cited

U.S. PATENT DOCUMENTS

| | | | | |
|---|---|---|---|---|
| 4,699,132 A | * | 10/1987 | Carville | 128/876 |
| 5,012,821 A | * | 5/1991 | Tarver | 128/876 |
| 5,551,447 A | * | 9/1996 | Hoffman et al. | 128/876 |
| 5,664,844 A | * | 9/1997 | Greene | 297/485 |
| 5,807,218 A | * | 9/1998 | Nagatomo | 128/876 |
| 5,896,859 A | * | 4/1999 | Carroll | 128/845 |
| 5,943,705 A | * | 8/1999 | Sink | 2/338 |
| 6,725,865 B2 | * | 4/2004 | Chapman | 128/876 |

* cited by examiner

Primary Examiner—Fadi H. Dahbour
(74) Attorney, Agent, or Firm—Ronald E. Smith; Smith & Hopen, P.A.

(57) ABSTRACT

An adjustable strap includes a flat base having a pair of upstanding tabs and a pair of rectangular slots. A flat rod has opposite ends captured in slots formed in the tabs. A lock member includes a strap-engaging locking part. A harness strap first loop captures a harness swivel hook assembly including a lanyard hook swivelly mounted to a swivel base and a second loop that captures a leading end of the flat base. A handle strap loop engages the second slot. An ambulator swivel hook assembly includes a lanyard hook swivelly mounted to a swivel base that is captured by an ambulator strap loop. The ambulator strap extends through the first rectangular slot, over the flat rod, and back through the first rectangular slot. The leading end cannot pass through the first rectangular slot, preventing the strap from disengaging from the base.

8 Claims, 2 Drawing Sheets

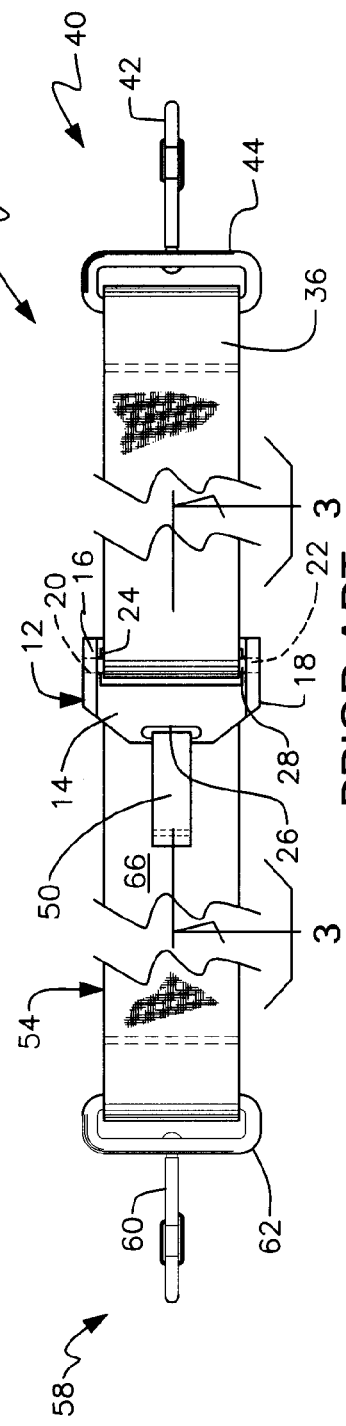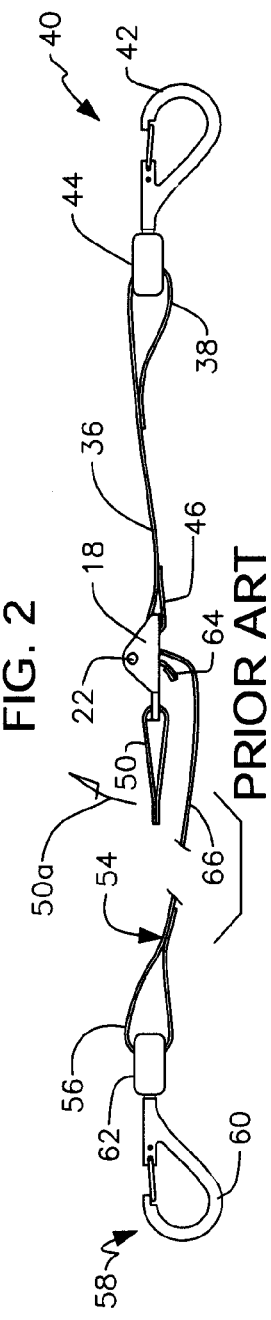

ADJUSTABLE STRAP FOR AMBULATOR

BACKGROUND OF INVENTION

1. Field of the Invention

This invention relates to ambulators. More particularly, it relates to an adjustable strap for an ambulator that is easy to tighten and release.

2. Description of the Prior Art

U.S. Pat. No. 5,112,044 to the present inventor discloses a harness worn by patients that facilitates caregivers in their efforts to help a patient from a bed onto a chair or vice versa, from a bed into a standing position, or vice versa, and so on. Pending U.S. patent application Ser. No. 09/681,808, filed Jun. 08, 2001, also to the present inventor, further discloses an ambulator having utility in connection with such harness.

The strap disclosed in the pending patent application for retaining the patient in the harness is easy to tighten but it is not easy to loosen.

What is needed, then, is an adjustable strap that is easy to tighten and equally easy to loosen.

However, in view of the prior art taken as a whole at the time the present invention was made, it was not obvious to those of ordinary skill how the identified need could be fulfilled.

SUMMARY OF INVENTION

The long-standing but heretofore unfulfilled need for an improved adjustable strap assembly is now met by a new, useful, and non-obvious invention. The novel adjustable strap assembly extends between a harness worn by an individual and the frame of an ambulator. More particularly, there are four of such adjustable straps, each having a leading end releasably engaged to the harness and a trailing end releasably engaged to the ambulator frame.

The novel adjustable strap includes a flat base and a pair of longitudinally-extending upstanding tabs formed integrally with the base in transversely spaced apart relation to one another. A slot is formed in each of the tabs.

A first transversely disposed rectangular slot is formed in the flat base, substantially centrally thereof. A second transversely disposed slot, having less extent than the first transversely disposed slot, is formed in a trailing end of the flat base.

A flat rod has opposite ends that are captured in the slots. A locking part adapted to engage a strap is formed integrally with the flat rod and extends therefrom along the extent thereof.

A truncate harness strap has a first loop formed in a leading end thereof. The first loop is adapted to capture a harness swivel hook assembly. The harness swivel hook assembly includes a lanyard hook that is swivelly mounted to a swivel base and a second loop formed in a trailing end thereof. The second loop is adapted to capture the first rectangular slot formed in the flat base.

A handle strap has a single loop that extends through the second rectangular slot.

An ambulator frame swivel hook assembly includes a lanyard hook that is swivelly mounted to a swivel base. An ambulator strap has a trailing end, an elongate medial part, and a leading end. A loop is formed in the trailing end and captures the swivel base of the ambulator frame swivel hook assembly.

The ambulator strap leading end is thicker than the elongate medial part. The elongate medial part follows a path of travel that extends through the first rectangular slot, over the flat rod, and back through the first rectangular slot. The leading end is too thick to pass through the first rectangular slot. Thus, the leading end serves as a stop means that prevents the ambulator strap from disengaging from the flat base.

The primary object of this invention is to provide an adjustable strap for use with an ambulator harness that is easy to tighten and loosen.

A closely related object is to provide an easily adjustable strap having structural simplicity so that it is economical to manufacture.

These and other objects will become apparent as this disclosure proceeds. The invention includes the features of construction, arrangement of parts, and combination of elements set forth herein, and the scope of the invention is set forth in the claims appended hereto.

BRIEF DESCRIPTION OF DRAWINGS

For a fuller understanding of the nature and objects of the invention, reference should be made to the following detailed description, taken in connection with the accompanying drawings, in which:

FIG. 1 is a top plan view of an adjustable strap of the prior art;

FIG. 2 is a side elevational view of the adjustable strap of FIG. 1;

FIG. 3 is a sectional view of the prior art locking means taken along line 3—3 in FIG. 1;

DETAILED DESCRIPTION

Figure 4:
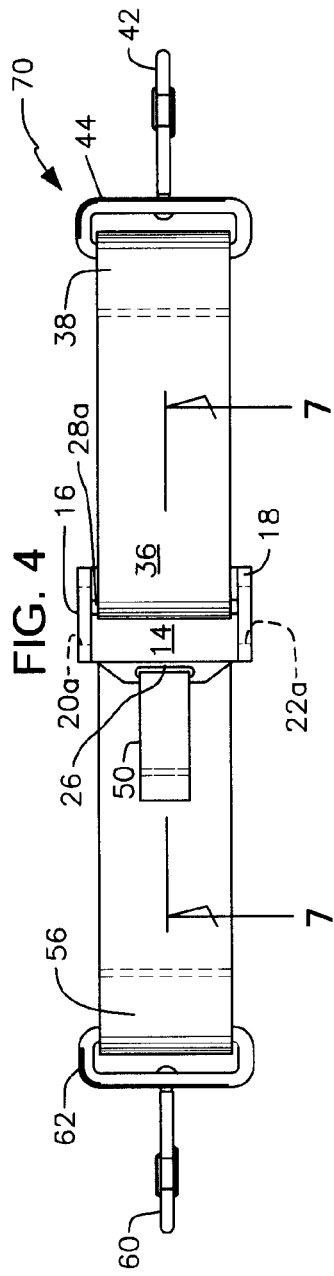
FIG. 4 is a top plan view of the novel adjustable strap.

Referring now to prior art FIGS. 1–3, it will there be seen that an adjustable strap assembly of the prior art is denoted as a whole by the reference numeral 10. Four (4) of such straps are used with the novel ambulator as is best understood in connection with pending U.S. patent application Ser. No. 09/681,808, filed Jun. 08, 2001 by the present inventor, entitled Ambulator and Gate Harness System, which disclosure is hereby incorporated by reference into this disclosure.

Assembly 10 includes base 12 having flat wall 14 and a pair of longitudinally disposed upstanding tabs 16, 18 integrally formed therewith at opposite ends thereof. Apertures 20 and 22 are formed in said tabs 16, 18, respectively.

Transversely disposed rectangular slot 24 is formed in flat wall 14, substantially centrally thereof. Transversely disposed slot 26, having less extent than first slot 24, is formed in a trailing end of flat wall 14.

As used herein, the leading end of the adjustable strap assembly is the end that is releasably connected to the harness worn by a patient and the trailing end of the adjustable strap assembly is the end that is releasably connected to the ambulator.

Transversely disposed rectangular slot 24 is hereinafter referred to as the first rectangular slot and transversely disposed rectangular slot 26 is hereinafter referred to as the second rectangular slot.

Post 28 has its opposite ends captured in apertures 20, 22. Lock member 30 (FIG. 3) has a tubular part 32 that ensleeves post 28 and a locking part 34 that extends from said tubular part 32 along the extent thereof.

Harness strap 36 is truncate in extent and includes a first or leading loop 38 that captures harness swivel hook assembly 40. Assembly 40 includes lanyard hook 42 that is swivelly mounted on swivel base 44. Harness strap 36 further includes a second or trailing loop 46 that engages first rectangular slot 24.

Handle strap 50 includes a single loop that extends through second rectangular slot 26.

Ambulator strap 54 includes trailing loop 56 that captures ambulator frame swivel hook assembly 58. Assembly 58 includes lanyard hook 60 that is swivelly mounted to swivel base 62.

Ambulator strap 54 has a leading end 64 that is thickened by several folds formed in said leading end that are sewn or otherwise held in place.

The elongate intermediate part 66 of ambulator strap 54 follows a path of travel that extends through first rectangular slot 24, over tubular part 32, and back through first rectangular slot 24. Thickened leading end 64 cannot pass through first rectangular slot 24 and thus serves as a stop member that prevents ambulator strap 54 from disengaging from base 12.

FIG. 2 depicts assembly 10 after it has been fully loosened, i.e., after ambulator strap 54 has effectively been lengthened. Tightening is accomplished by pulling on thickened leading end 64. However, loosening ambulator strap 54 is problematic. Specifically, lifting handle strap 50 as indicated by directional arrow 50a in FIG. 2 should release the grip between locking part 34 and adjustable strap 54 but in practice the user must struggle for quite some time before the loosening can be accomplished.

Figure 5:
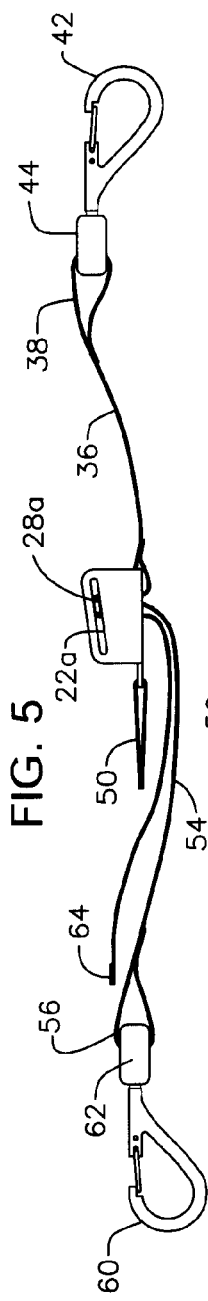
FIG. 5 is a first side elevational view of the novel adjustable strap.
Figure 6:
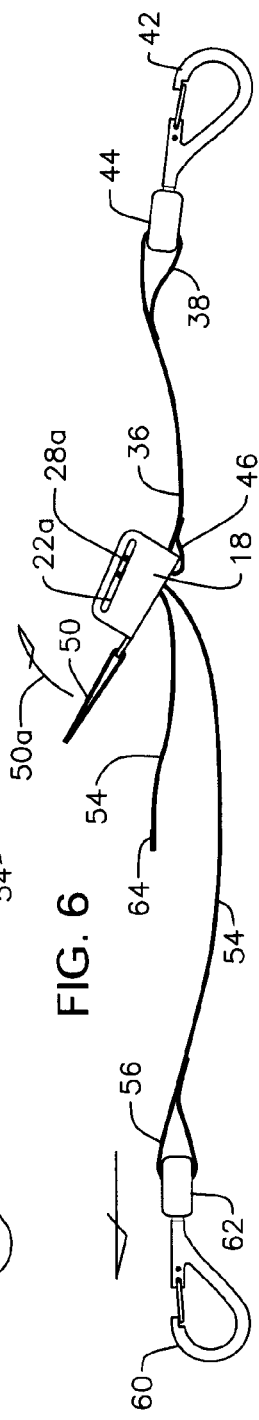
FIG. 6 is a second side elevational view of the novel adjustable strap.
Figure 7:
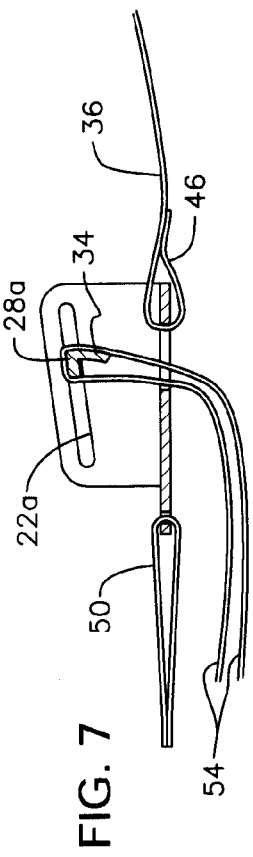
FIG. 7 is a sectional view taken along line 7—7 in FIG. 4.

FIGS. 3–7 depict novel adjustable strap assembly 70. It shares a common construction in many respects, as indicated by the similar reference numerals, with prior art adjustable strap assembly 10, but with the exceptions that prior art apertures 20, 22 are eliminated and replaced with slots 20a, 22a and prior art post 28 is eliminated and replaced with flat rod 28a having opposite ends that slide in said slots 20a, 22a. Prior art tube 32 is eliminated and locking part 34 is formed integrally with flat rod 28a. Lifting handle strap 50 as indicated by directional arrow 50a in FIG. 6 releases the grip between locking part 34 and adjustable strap 54 so that loosening of said strap 54 is no longer problematic.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An adjustable strap assembly having a harness strap releasably connected to an ambulator harness and having an ambulator strap releasably connected to an ambulator frame, comprising:

a flat base having a pair of longitudinally extending tabs formed integrally with said flat base in transversely spaced apart relation to one another;

a first rectangular slot formed in a leading end of said flat base;

a second rectangular slot formed in a trailing end of said base;

a transversely disposed locking means supported at its opposite ends by said tabs, said locking means adapted to releasably engage said ambulator strap;

said harness strap having a first loop formed in a leading end thereof;

said first loop adapted to engage a harness swivel hook assembly;

said harness strap further including a second loop formed in a trailing end thereof;

said second loop adapted to engage said first rectangular slot formed in said leading end of said flat base;

a handle strap having a single loop that extends through said second rectangular slot;

an ambulator swivel hook assembly;

said ambulator strap interconnecting said ambulator swivel hook assembly and said flat base;

said ambulator strap part following a path of travel that extends through said first rectangular slot, over said locking means, and back through said first rectangular slot;

said locking means including transversely disposed flat rod having opposite ends connected to said tabs;

a locking part formed integrally with said flat rod, said locking part extending from said flat rod along the extent thereof; and said locking part adapted to engage said ambulatory strap.

2. The adjustable strap assembly of claim 1, further comprising:

a slot formed in each of said tabs;

said flat rod having opposite ends captured in said slots.

3. The adjustable strap assembly of claim 2, further comprising:

said first rectangular slot being transversely disposed relative to a longitudinal extent of said adjustable strap assembly.

4. The adjustable strap assembly of claim 3, further comprising:

said second rectangular slot being transversely disposed relative to a longitudinal extent of said adjustable strap assembly, and said second rectangular slot having less extent than said first rectangular slot.

5. The adjustable strap assembly of claim 4, further comprising:

said harness swivel hook assembly including a lanyard hook and a swivel base, said lanyard hook being swivelly mounted to said swivel base.

6. The adjustable strap assembly of claim 5, further comprising:

said ambulator swivel hook assembly including a lanyard hook that is swivelly mounted to a swivel base.

7. The adjustable strap assembly of claim 6, further comprising:

said ambulator strap having a trailing end, an elongate medial part, and a leading end;

a loop formed in said trailing end of said ambulator strap, said loop adapted to engage said swivel base of said ambulator frame swivel hook assembly.

8. The adjustable strap assembly of claim 7, further comprising:

said ambulator strap having a leading end that is thicker than said elongate medial part;
said leading end being too thick to pass through said first rectangular slot, said leading end thereby serving as a stop means that prevents said ambulator strap from disengaging from said flat base.

* * * * *